US006478425B2

(12) United States Patent
Trajkovic et al.

(10) Patent No.: US 6,478,425 B2
(45) Date of Patent: Nov. 12, 2002

(54) SYSTEM AND METHOD FOR AUTOMATICALLY ADJUSTING A LENS POWER THROUGH GAZE TRACKING

(75) Inventors: Miroslav Trajkovic, Ossining, NY (US); Srinivas Gutta, Buchanan, NY (US); Antonio J. Colmenarez, Peekskill, NY (US)

(73) Assignee: Koninlijke Phillip Electronics N. V., Eindhoven (NL)

( * ) Notice: Subject to any disclaimer, the term of this patent is extended or adjusted under 35 U.S.C. 154(b) by 10 days.

(21) Appl. No.: 09/752,742

(22) Filed: Dec. 29, 2000

(65) Prior Publication Data

US 2002/0113943 A1 Aug. 22, 2002

(51) Int. Cl.⁷ .................................................. A61B 3/14
(52) U.S. Cl. ...................................................... 351/209
(58) Field of Search ................................ 351/209, 210, 351/155, 57; 359/407, 422, 432, 696, 362, 368

(56) References Cited

U.S. PATENT DOCUMENTS

| 5,220,361 | A | * | 6/1993 | Lehmer et al. ............. 351/226 |
| 5,861,940 | A | | 1/1999 | Robinson et al. ........... 351/221 |
| 5,867,308 | A | | 2/1999 | Pensel et al. ................ 359/368 |
| 5,892,566 | A | | 4/1999 | Bullwinkel ................. 351/210 |
| 5,980,041 | A | | 11/1999 | Strachan ..................... 351/210 |
| 6,079,829 | A | | 6/2000 | Bullwinkel ................. 351/210 |
| 6,152,563 | A | | 11/2000 | Hutchinson et al. ........ 351/209 |

OTHER PUBLICATIONS

Stiefelhagen, R., et al., *A Model–Based Gaze Tracking System*, International Journal of Artifical Intelligence Tools, vol. 6, No. 2, pp. 193–209 (1997).

(List continued on next page.)

*Primary Examiner*—George Manuel
(74) *Attorney, Agent, or Firm*—Gregory L. Thorne

(57) ABSTRACT

The present invention relates to a device containing an automatic zoom lens, and more particularly to a zoom lens that is controlled by a processor that is linked to a gaze tracking system. As a user looks onto an object through the device, the gaze tracking system collects data relating to the position of each eye of the user. This eye position data is input into the processor where the focal point of the user is determined. The processor then adjusts the zoom lens to zoom in or out onto the object based on either a predetermined or user input zoom factor.

16 Claims, 4 Drawing Sheets

OTHER PUBLICATIONS

Heinzmann, J., et al., *3D Facial Pose and Gaze Point Estimation Using a Robust Real–Time Tracking Paradigm*, Proceedings of the Third International Conference on Automatic Face and Gesture Recognition, sponsored by IEEE Computer Society Technical Committee on Pattern Analysis and Machine Intelligence, Apr. 14–16, 1998 (Nara, Japan), pp. 142–147.

Jacob, R., *The Use of Eye Movements in Human–Computer Interaction Techniques: What You Look at is What you Get*, ACM Transactions on Information Systems, vol. 9, No. 3, pp. 152–169, Apr. 1991.

Baluja, S., *Non–Intrusive Gaze Tracking Using Artificial Neural Networks*, CMU Technical Report, CMU–CS–94–102.

Product Specification for a 13M*X* Series Motorized Zoom Lens.

Document entitled: *Eyelink Gaze Tracking*, printed from website http://www.smi.de/el/elsys.htm.

Document entitled: *Eyelink Gaze Tracking*, printed from website http://www.smi.de/el/elspecs.htm.

Document entitled: *Eyelink Gaze Tracking*, printed from website http://www.smi.de/el/elintro.htm.

Document entitled: *Eyelink Gaze Tracking*, printed from website http://www.smi.de/el/elapps.htm.

Document entitled: *2D VOG–Video–Oculography*, printed from website http://www.smi.de/2d/2intro.htm.

Document entitled: *2D VOG Video–Oculography*, printed from website http://www.smi.de/2D/2dsys.htm.

Introduction and Present–Day Eye–Gaze Tracking Techniques documents printed from the website http://www.d-iku.dk/~panic/eyegaze.

Brooker et al: "A helmet mounted display system with active gaze control for visual telepresence," Mechatronics, Pergamon Press, Oxford, GB, vol. 9, NR. 7, pp. 703–716.

* cited by examiner

SYSTEM AND METHOD FOR AUTOMATICALLY ADJUSTING A LENS POWER THROUGH GAZE TRACKING

BACKGROUND OF THE INVENTION

1. Field of the Invention

The present invention relates to a system that changes the magnification factor of an optical device based on the point of focus of a user, and more particularly to a system that changes the magnification factor by determining the intersection of gaze lines of the user.

2. Description of the Related Art

Optical devices such as binoculars and cameras often contain systems that can zoom in and zoom out to adjust the magnification of a viewed object. The systems incorporated into these devices change the magnification factor or zoom ratio by moving the zoom lens by either manual adjustment or by a motor. The motorized systems typically incorporate a dial or push button system or some other electronic control linked to the motor, such as a stepper motor, that moves the lenses to adjust the zoom ratio. By the push of a button a signal is sent to a control unit that activates the stepper motor. The stepper motor is mechanically linked to the lens system and adjusts the lenses to zoom in or zoom out at the control of the user. One particular manufacturer of motorized zoom lenses is Pelco, the operations and specifications of which can be viewed at their web site <<http://www.pelco.com>>.

One problem of the existing motorized zoom lenses is that they all require the use of the hands of the user to control the zoom.

In a different field that is also related to the present invention, there are various techniques for tracking the direction of movement of the human eye, generally referred to as gaze tracking. Gaze tracking concerns detection or measurement of the angular movement and position of the eye. A document that describes various known gaze tracking techniques is *Eye Controlled Media: Present and Future State,* by Theo Engell-Nielsen and Arne John Glenstrup (1995), which may be found at <http://www.diku.dk/~panic/eyegaze>>, and is hereby incorporated herein by reference. The various techniques determine the focal point of a user by tracking the movements of the head and/or eyes of the user. The movement of an eye can be detected by use of the three present day techniques: detecting reflected light off of different parts of the eye, measuring electric potential differences of the adjacent skin as the eye moves, and utilizing specially designed contact lenses.

Commercially available gaze tracking systems determine the direction that a person is looking and then use the data regarding the gaze angle for a related purpose. For example, certain gaze tracking systems control the movement of a cursor on a computer screen based on where the person is looking. One manufacturer of gaze tracking systems is SensoMotoric Instruments, and their commercially available equipment may be seen at <<http://www.smi.de>>. By mounting detectors, e.g. cameras and/or other sensors, onto or near the eyes of a user, the system detects the small angular movements of the eye and moves the cursor based on the angular movement of the eye. The SensoMotoric Instrument systems also disclose analysis of detected eye movement for medical diagnostic purposes.

Thus, gaze tracking systems have heretofore been limited in their applications to analysis of eye movement itself or to the simple application of moving a cursor such that it corresponds to the detected gaze angle of the eye.

SUMMARY OF THE INVENTION

It is an aspect of the present invention to provide a method and system for controlling a magnification factor of an optical device through use of a gaze tracking system.

It is another aspect of the present invention to additionally incorporate a voice recognition system to control basic functions of the zoom lens.

The invention comprises an optical device having a gaze tracking system that automatically adjusts an optical parameter based on a gaze distance parameter calculated using the gaze angle received from the gaze tracking system.

In one embodiment of the invention, an optical device comprises at least one adjustable optical element, gaze tracking input sensors, a motor that interfaces with the at least one optical element and is able to move the at least one element, and a control unit that supports gaze tracking and related gaze distance algorithms, as well as software that provides control input to the motor. The gaze tracking input sensors receive input regarding the gaze angle of the eyes, which is transmitted to the control unit. Gaze tracking algorithm in the control unit determines the gaze angle of the eyes, and gaze distance algorithm use the calculated gaze angle to calculate the gaze distance, that is, the distance from the viewer to the point where the eyes are focused or gazing. The calculated distance is then used to calculate an adjustment of the at least one optical element, and a control signal is sent to the motor to make the adjustment in position of the at least one optical element.

In another preferred embodiment, a pair of binoculars comprises zoom lenses, one or more gaze tracking cameras, a stepper motor that interfaces with the zoom lenses, and a control unit that supports gaze tracking and related gaze distance algorithms, as well as software that provides control input to the stepper motor. The gaze tracking cameras capture images of the position of one or more features of the eyes that is used by the gaze tracking algorithms in the control unit to determine the gaze angle of the eyes. The gaze angle is further processed by the gaze distance algorithm to determine the gaze distance. The gaze distance is further used to determine the appropriate position of the zoom lenses to focus at the gaze distance, and an appropriate control signal is provided by the processor to the stepper motor to move the zoom lenses to that position.

In yet another preferred embodiment, a camera comprises a zoom lens, one or more gaze tracking cameras, a stepper motor that interfaces with the zoom lens, and a control unit that supports gaze tracking and related gaze distance algorithms, as well as software that provides control input to the stepper motor. The gaze tracking cameras capture images of the position of one or more features of the eyes that is used by the gaze tracking algorithm in the control unit to determine the gaze angle of the eyes. The gaze angle is further processed by the gaze distance algorithm to determine the gaze distance. The gaze distance is further used to determine the appropriate position of the zoom lens to focus the camera at the gaze distance, and an appropriate control signal is provided by the processor to the stepper motor to move the zoom lens to that position.

Thus, among other things, the present invention provides an automatic adjustment to the optical element based on the gaze angle and corresponding focus point of the user. In addition, the present invention may additionally incorporate a voice recognition system whereby a voice command is required as input before the automatic adjustment is undertaken. For example, a voice command may be required before the gaze tracking algorithm and the subsequent processing and control of the optical element or lenses will be initiated. Alternatively, such processing may be engaged and running, but the final control command to the motor requires a voice input.

BRIEF DESCRIPTION OF THE DRAWINGS

The above and other aspects, features and advantages of the present invention will become more apparent from the following detailed description when taken in conjunction with the accompanying drawings in which.

DETAILED DESCRIPTION OF INVENTION

Preferred embodiments of the present invention will be described herein below with reference to the accompanying drawings. In the following description, well-known functions or constructions are not described in detail since they would obscure the invention in unnecessary detail.

Figure 1:
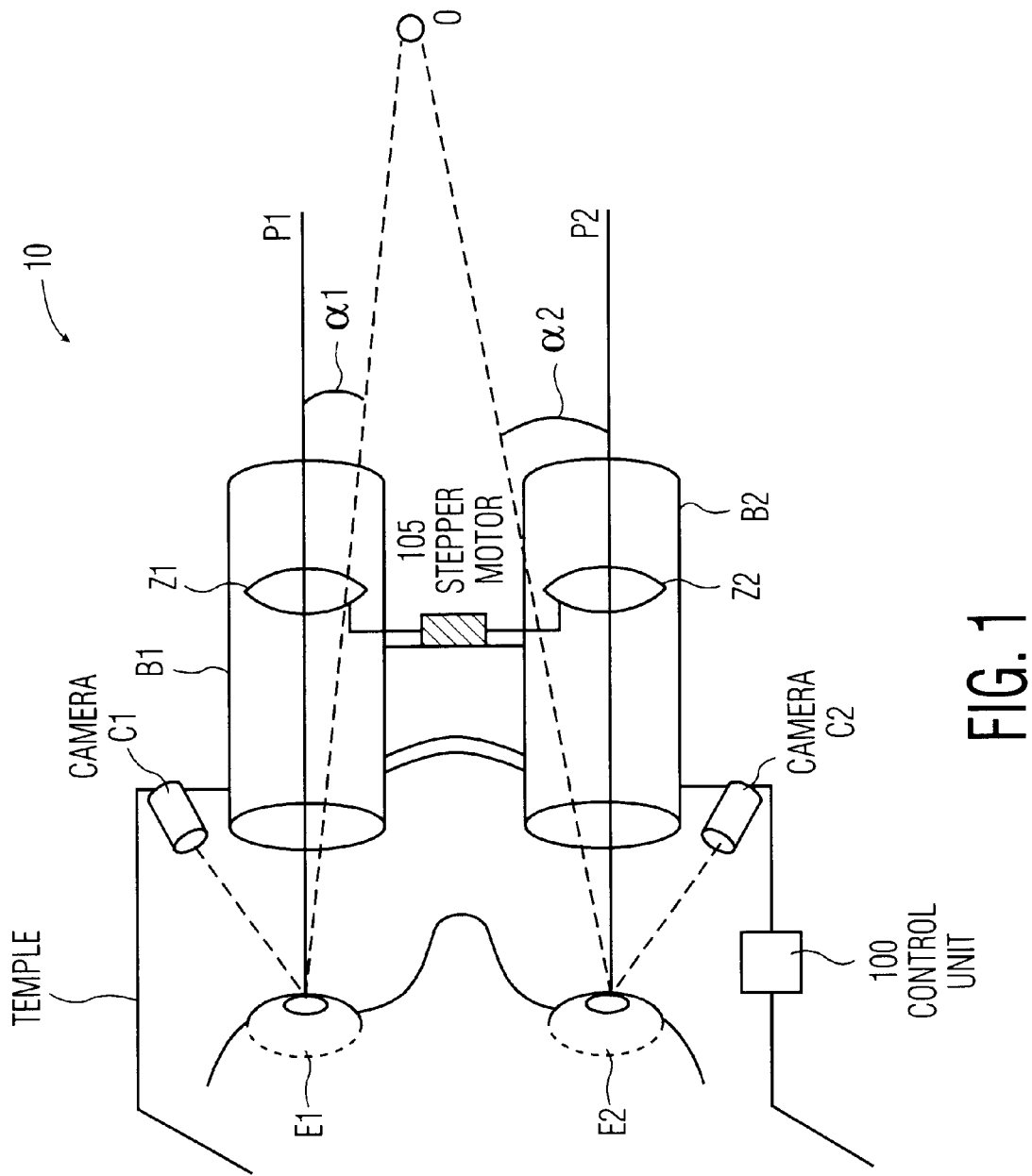
FIG. 1 is a diagram of a system for automatically zooming a lens according to an embodiment of the present invention.

FIG. 1 shows a user looking through an embodiment of the invention that comprises a binocular system 10. As shown in FIG. 1, a gaze tracking sub-system is comprised of two cameras, C1 and C2, a control unit 100 and related software stored therein. Eyes E1 and E2 of the user are shown. Also shown are monocular B1 and monocular B2, which make up the binoculars. A stepper motor 105 is shown connected to zoom lenses Z1 and Z2. As described further below, control unit 100 includes software that generates control signals for control unit 100.

Control unit 100 may comprise, for example, a processor having associated RAM and ROM that is mounted directly to the binocular system 10, that is interconnected with wires (not shown) to cameras C1, C2 to receive gaze tracking information data therefrom. Control unit 100 is also interconnected with a wire or wires (not shown) with stepper motor 105 to provide commands thereto and receive position data of the zoom lens. Alternatively, control unit 100 may comprise a separate unit not mounted to the binoculars that is interconnected with the cameras C1, C2 and stepper motor 105 with a wire or wireless connection.

Cameras C1, C2 provide video data relating to the angular movement of the eyes E1, E2 (gaze tracking data) to the control unit 100. The gaze tracking data comports with one of the gaze tracking techniques as known in the art and which is stored in the form of a gaze tracking algorithm in software of control unit 100. The control unit 100 thus processes the received gaze tracking data to determine a gaze angle(s) with respect to normal (i.e., the axis when the person is looking straight ahead or, equivalently, along the axis of the monoculars B1, B2). The gaze angle determined is used by the control unit 100, along with other input, such as the separation of the eyes E1, E2 of the user, to calculate the distance to the point (for example, point O shown in FIG. 1) that the user is focused on (the focal distance of the user). The distance between the eyes may be provided as a separate input to the control unit 100. For example, when the monoculars B1, B1 are adjusted to a viewer's eyes, the eyes are generally aligned with the central axis of each monocular. Thus, the distance between the viewer's eyes is substantially equal to the separation of the central axes of the monoculars, which is a function of the setting of the adjustment mechanism between the monoculars B1, B2. A sensor that interfaces with the adjustment mechanism between monoculars B1, B2 may provide the control unit 100 with a measure of the adjustment setting between the monoculars B1, B2. The control unit 100 may thus determine the eye separation using, for example, a table that provides the distance between the central angles of the monoculars (and thus the viewer's eyes) as a function of the setting of the adjustment mechanism.

Alternatively, the image provided by the cameras C1, C2 may be used in an analogous manner. For example, in an eye measurement mode, monoculars B1, B2 may be adjusted such that each eye is centered in the image provided by the respective camera C1, C2. The control unit 100 has a pre-stored table that gives eye separation distance as a function of the setting of the adjustment mechanism between the monoculars B1, B2 when the eyes are so centered in the image. The adjustment setting is sent to the control unit 100 when the eyes are centered in the image by a sensor that interfaces with the adjustment mechanism. The control unit 100 uses the measurement to look up the eye separation distance.

As noted, control unit 100 stores in memory the current position of lenses Z1, Z2. The control unit may keep track of the lens position by maintaining a count of the number of steps and direction of steps by the stepper motor 105 (referred to as "zoom ticks") over time. Alternatively, a sensor that interfaces with the stepper motor and/or the lenses may be queried by the control unit 100 to provide current position of the lenses to the control unit 100. After calculating the focal distance of the user based on the gaze tracking data, control unit 100 then determines the position to which the zoom lenses Z1, Z2 must be moved to provide a zoom focus on the focal point by the binoculars. The control unit 100 outputs step or zoom tick commands to the stepper motor 105 that move the lenses Z1, Z2 from the current position to the user focal distance. Thus, the binoculars automatically focus to the distance and thus the point at which the user is gazing.

Figure 1A:
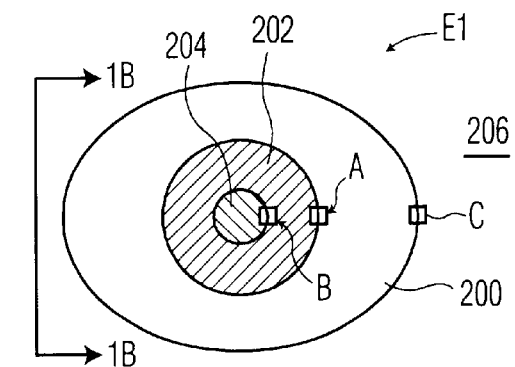
FIG. 1A is a diagram depicting several elements of a human eye.
Figure 1B:
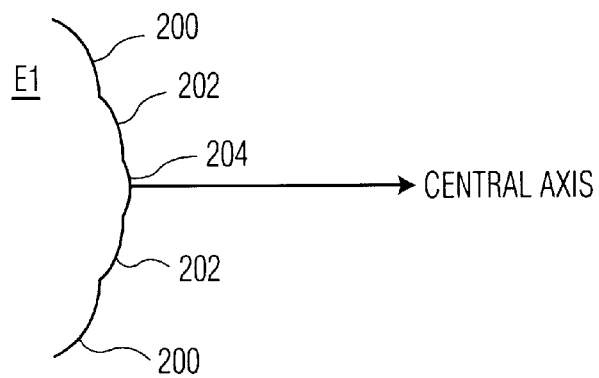
FIG. 1B is a side view of a human eye shown in FIG. 1A.

FIG. 1A depicts a front view of a user's eye E1, having a white sclera portion 200, a (typically) darker iris portion 202 and a central pupil portion 204. The eye in FIG. 1A is shown centered, for example, when the head is level and the eye is looking at the level horizon along an axis, referred to as the central axis of the user. Thus, for FIG. 1A, the central axis of the user is straight out of the page. FIG. 1B is a side view of the eye that shows a second perspective of the central axis of the user.

As noted above, for gaze tracking, a camera, such as camera C1 of FIG. 1, provides images of eye E1, such as that shown in FIG. 1A, to control unit 100 for processing. As known in the art, the images of the eye are captured by camera C1 on pixels of a CCD array. Each pixel of the CCD array thus provides an intensity measurement for the corresponding portion of the captured image to the control unit.

Referring back to FIG. 1A, the pixels in the region of the image corresponding to point A (or any point on the border between the sclera portion 200 and the iris portion 202) will show a relatively great change in intensity between certain pixels. The same occurs for the pixels corresponding to point B (or any point on the border between the iris portion 202 and the pupil 204).

In addition, the control unit may determine a reference point, such as point C between the eye and the skin of the user's face 206. Point C may be detected, for example, by a change in intensity between the pixels of the sclera portion 200 and the user's skin 206. Point C is a fixed reference point on the user's head with respect to movement of the eye. The reference point C may be located at other points on the user's head within the field of view of the camera, and other points may be used to determine motion in two dimensions, as described below. The fixed reference point may also be a series of points, determined, for example, by an image recognition algorithm of a human head.

Figure 1C:
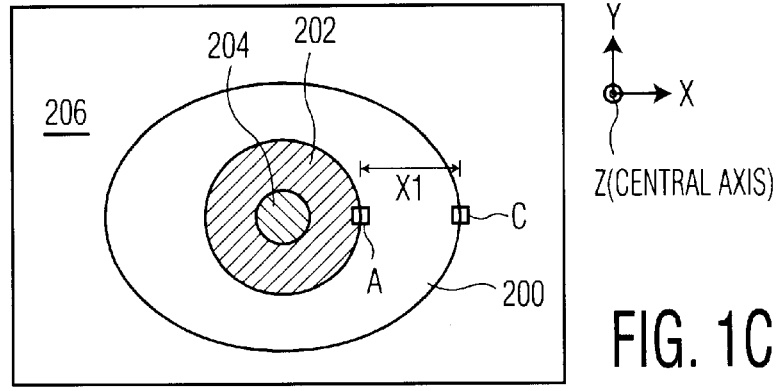
FIG. 1C is a diagram of an image of a human eye captured by a gaze tracking system.
Figure 1D:
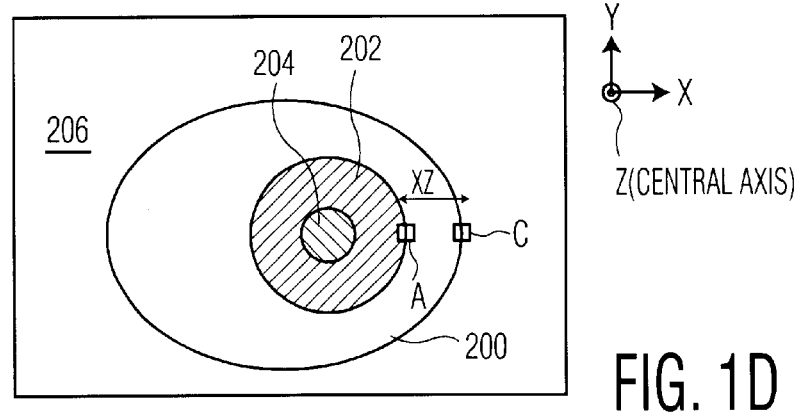
FIG. 1D is a diagram of an image of a human eye in a different position than in FIG. 1C.

In one technique of gaze tracking, the position of the eye with respect to the head is determined from the image. The principle of this gaze tracking technique is described with respect to FIGS. 1C and 1D. FIGS. 1C and 1D show two different images of the eye E1 at different gaze angles as recorded by camera C1 and sent to control unit in the form of digitized data from each pixel in the camera's CCD. FIG. 1C represents the eye looking straight ahead, i.e., along the central axis as defined above. Using the change in intensity between the iris portion 202, sclera portion 200 and the skin of the user's head 206 as described above, the control unit 100 determines points A (at the border of the iris portion 202 and the sclera portion 200) and point C (at the border of the sclera portion 200 and the skin 200) along the X axis as shown. Thus, the image distance X1 is determined by the control unit 100.

In FIG. 1D, the eye is gazing to the left (along the X axis) at a gaze angle with respect to the central axis. Thus, the point A in the image moves toward the point C as shown. By determining the positions of points A and C in the image of FIG. 1D (once again, by detecting the change in intensities between features of the eyes), the control unit 100 determines the distance X2.

The gaze angle of the eye E1 with respect to the central axis is a function of the change in X position, namely X1–X2. The function may be determined by the control unit 100 in a training program where displacement of the eye in the images (for example, as measured between points A and C) is detected and recorded for known gaze angles. (In the system of FIG. 1, for example, the gaze angle is zero where the eye is centered in the image, and the gaze angle is equal to the angular width of the monocular when gazing at the edge of the field of view. By capturing these two images in a training program, the control unit 100 may determine a linear correlation between displacement and gaze angle.) Using the data collected in the training program, the control unit 100 may extrapolate a gaze angle for a detected displacement in an image (such as X1–X2).

It is noted that the eye need not gaze along the X axis of the image as shown in FIG. 1D, but can lie at some angle with respect to the X and Y axis. The control unit 100 may have analogous processing that accommodates movement of the eye in both the X and Y direction (i.e., at any direction in the X–Y plane).

As known in the art, this and other techniques of gaze tracking have become highly sophisticated, in order to accommodate movement of the head, high resolution of small movements, fast response time, movement of the eye in two dimensions, etc. Typically, gaze tracking systems use high speed images in processing a gaze angle in order to accommodate these other variables and factors. In addition, a gaze angle for both eyes is determined. The following documents related to techniques of gaze tracking are hereby incorporated by reference: 1) U.S. Pat. No. 5,861,940 entitled "Eye Detection System For Providing Eye Gaze Tracking" to Robinson et al.; 2) U.S. Pat. No. 6,152,563 entitled "Eye Gaze Direction Tracker" to Hutchinson et al.; 3) Stiefelhagen, Yang & Waibel, A Model-Based Gaze Tracking System, International Journal of Artificial Intelligence Tools, Vol. 6, No. 2, pp 193–209 (1997); 4) Shumeet Baluja & Dean Pomerleau, "Non-intrusive Gaze Tracking Using Artificial Neural Networks", CMU Technical Report, CMU-CS-94-102; 5) Robert J. K. Jacob, "The Use Of Eye Movements In Human-Computer Interaction Techniques: What You Look At Is What You Get", ACM Transactions On Information Systems, Vol. 9, No. 3, pp 152–169 (April 1991); 6) Heinzmann and Zelinsky, "3-D Facial Pose And Gaze Point Estimation Using A Robust Real-Time Tracking Paradigm", Proceedings of the Third International Conference on Automatic Face and Gesture Recognition, sponsored by IEEE Computer Society Technical Committee on Pattern Analysis and Machine Intelligence, Apr. 14–16, 1998 (Nara, Japan), pp 142–147.

Alternatively, a commercially available system such as the SensoMotoric Instruments "EyeLink Gaze Tracking" system may be used. (As noted above, details regarding the Eyelink system and other systems of SensoMotoric Instruments may be found on their website, www.smi.de.) The Eyelink system provides the cameras and gaze tracking software, however, the software controls movement of a cursor on a display screen in response to the detected eye movement. Thus, if the Eyelink system is used, for example, it is adapted with a software subroutine that translates cursor position (output by the Eyelink gaze tracking system) back to angular position with respect to the central axis. Such a subroutine can be based on straightforward geometric and spatial relationships between a display and the user.

Figure 2:
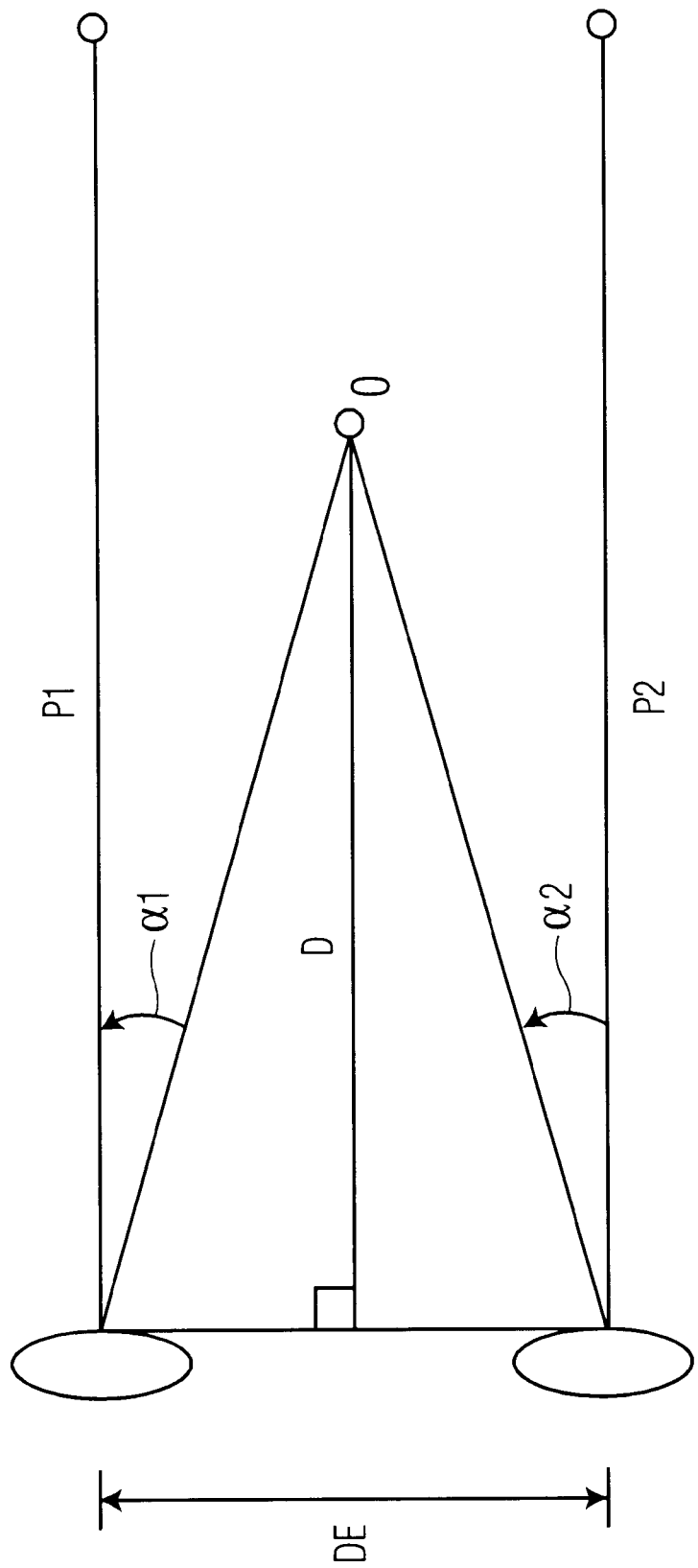
FIG. 2 is a geometric diagram of the system described in FIG. 1 according to an embodiment of the present invention.

Thus, whatever gaze tracking technique is used by the binocular system 10 of FIG. 1, the gaze tracking components (i.e., cameras C1, C2, control unit 100 and related software) fundamentally calculate a gaze angle of the eyes E1, E2 with respect to the central angle of the viewer. FIG. 2 represents eyes E1, E2 focusing or gazing at a point O in the distance. As represented in FIG. 2, eyes E1, E2 have gaze angles $\alpha 1$ and $\alpha 2$, respectively from axes P1 and P2, respectively. (Axes P1 and P2 represent central axes of eyes E1, E2, respectively.) FIG. 2 omits monoculars Z1, Z2 shown in FIG. 1 interposed between the viewer's eyes E1, E2 and point O. However, even with the monoculars interposed, the eyes E1, E2 gaze at angles $\alpha 1$, $\alpha 2$ at a virtual point O at a virtual distance D, as one skilled in the art of optics will readily recognize.

Also shown is distance De the distance between eyes E1 and E2. As noted above, distance De is known to the control unit 100, for example, by measuring the eye separation of a user or otherwise detecting the eye separation of the user as described above. Lines P1, P2 and D are lines perpendicular to the line connecting eyes E1 and E2. Once the control unit 100 calculates the gaze tracking angles $\alpha 1$ and $\alpha 2$ as described above, distance D is calculated to the first order by control unit 100 as follows:

$$D = \frac{De}{\tan\alpha1 + \tan\alpha2} \qquad \text{Eq. 1}$$

The control unit may use a look up table or a subroutine to calculate the tangents.

Once distance D is determined, the control unit 100 controls the stepper motor 105 to adjust the position of the zoom lenses Z1, Z2 so that there is an automatic zoom focus of the default distance $d_0$. The zoom focal length f corresponding to the default distance $d_0$ may be calculated as:

$$f = \frac{D}{d_0} f_h \qquad \text{Eq. 2}$$

where do is a default zoom distance at which the object will appear, $f_h$ is the focal length of the user's (human) optical system. Once calculated, the control unit 100 sends control signals to the stepper motor 105 to move the zoom lenses Z1, Z2 such that the optical system has focal length f. The actual position is a function of the optics of the system; a look-up table of zoom lens position versus focal length of the particular optical system may be programmed into the control unit 100.

The control unit 100 can further move the zoom lenses Z1, Z2 so that the object focused on by the viewer at the distance D is zoomed in or out by additional increments with respect to the initial default zoom distance. The user may input the incremental distances in a calibration process that relates the additional increments to camera focal length. Once calibrated, the zoom increments correspond to a "zoom tick" or step of the stepper motor 105 as described above. The relation between focal lengths f and zoom ticks z is given, for example, by:

$$f = \frac{f_0}{1 + a_0 z + a_1 z^2} \qquad \text{Eq. 3}$$

where $a_0$, $a_1$, and $f_0$ are calibration parameters that can be provided to the user to provide a calibration per zoom tick. The focal lengths corresponding to zoom ticks over the range of movement of the lenses Z1, Z2 may be stored in a look-up table in the control unit 100, for example. Alternatively, the look-up table may correlate the zoom tick to the position of lenses Z1, Z2 (the "zoom tick position") that provides the corresponding focal length in the optical system.

The zoom ticks provide a way for the user to provide additional zooming or fine adjustment after the lenses Z1, Z2 are automatically moved such that the object gazed upon at distance D is zoomed to the default distance do. A zoom tick input corresponding to a zoom inward or a zoom outward instructs the control unit 100 to move the lenses Z1, Z2 to the next zoom tick position either inward or outward. The control unit 100 uses the look-up table to determine the adjacent zoom tick position either inward or outward to the current position of the lenses Z1, Z2 (i.e., the position corresponding to default distance $d_0$) The control unit 100 provides the stepper motor 105 to move the lenses Z1, Z2 to the zoom tick position.

After the lenses Z1, Z2 have been moved to focus at the default distance $d_0$, a zoom tick may be input to the system by the user manually using a button or alternatively via a voice input. In the latter case, a microphone is included on the binocular system 10 that interfaces with the control unit 100. Control unit 100 may have voice recognition software that recognizes, for example, the word "zoom in" or "zoom out". Each time the user says "zoom in", for example, the control unit 100 moves the lenses Z1, Z2 inward to the next zoom tick position. Each time the user says "zoom out", the control unit 100 moves the lenses Z1, Z2 outward to the next zoom tick position. In addition, the initial automatic zooming of the object gazed upon at distance D to the default zoom distance $d_0$ may first require a user input, such as the spoken word "zoom". Subsequent fine tuning of the default zoom, or further zooming in or out for other reasons in zoom tick increments may be undertaken using the "zoom in" or "zoom out" commands described above.

In addition, such a voice recognition feature may be used in alternative manners with the binocular system 10 of FIG. 1. For example, the voice recognition software may recognize spoken numbers and the words "feet", "meters" or other dimensions. Thus, the control unit 100 recognizes a desired zoom distance spoken by the user, such as "ten feet". The control unit 100 uses the same equation given above, namely:

$$f = \frac{D}{d} f_h \qquad \text{Eq. 4}$$

where D represents the gaze distance of the object as before and d refers to the spoken zoom distance desired by the user, in this example, ten feet. Control unit 100 determines the corresponding focal length f using the above equation and then determines the position of lenses Z1, Z2 corresponding to the focal distance (using, for example, a look-up table that correlates focal length of the optical system to lens position). Once the control unit 100 determines the corresponding lens position, it provides control signals to the stepper motor 105 to move the lenses to the position, thus zooming the object to ten feet, for example. Such a feature may be in addition to the automatic default zooming and/or zoom tick zooming described above.

Figure 3:
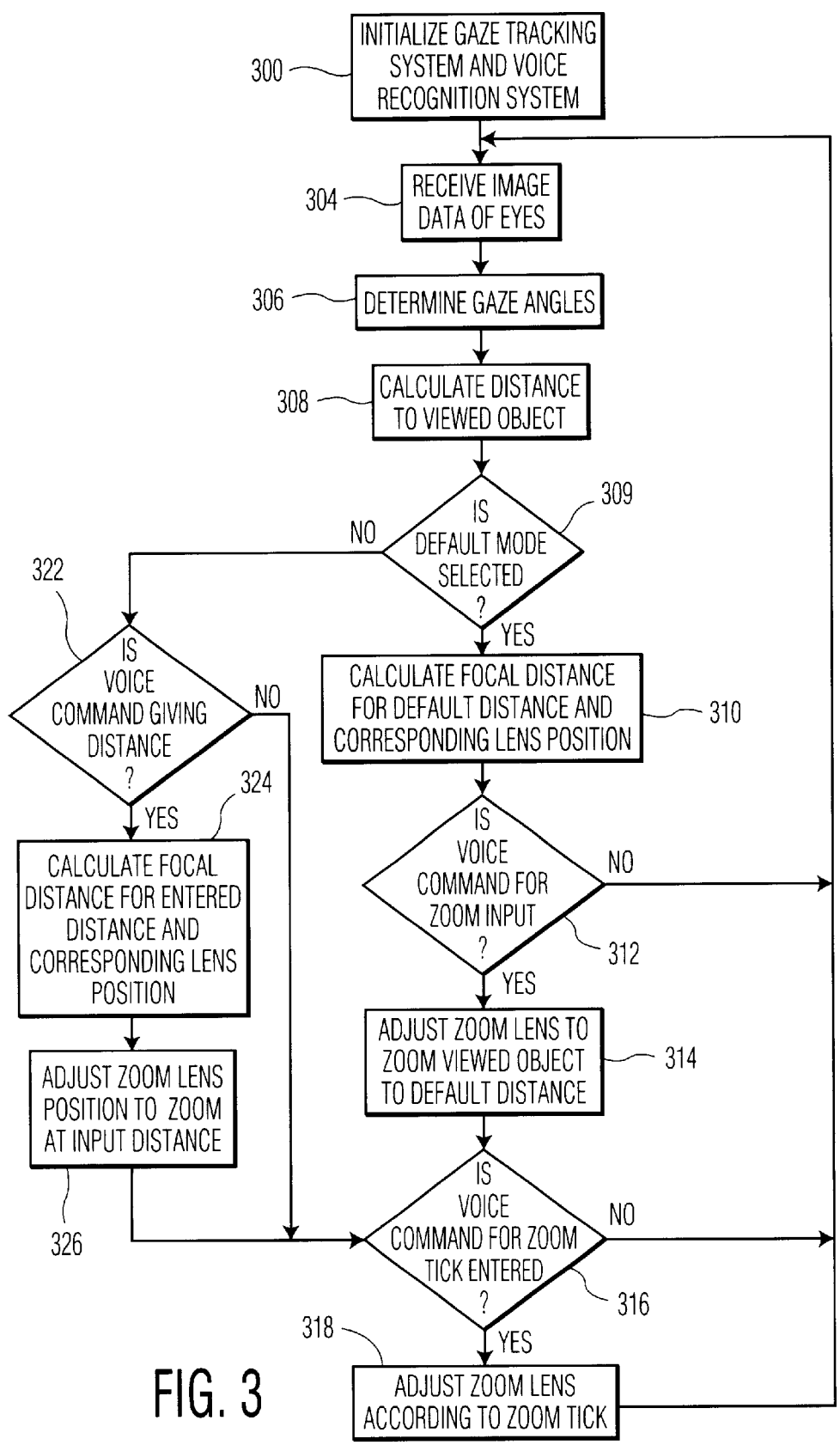
FIG. 3 is a flow chart showing the operation of the system according to an embodiment of the present invention.

The processing by control unit 100 of a comprehensive embodiment of the above-described binocular system 10 is thus described with reference to FIG. 3 (referring to components and distances as shown in FIGS. 1 and 2) as follows. In step he gaze tracking and voice recognition system is initialized. This step may include, for example, detecting and determining distance between the eyes De. Control unit 100 receives image data of the eyes E1, E2 from C1 and C2 as the user looks at object in step 304 and determines gaze angles α1, α2 of eyes E1, E2 using a gaze tracking technique in step 306. Using the gaze angles, the control unit 100 calculates the distance D to the object O in step 308, for example, using Eq. 1 above.

The control unit then determines whether a default mode is selected by the user in step 309. If yes, control unit 100 in step 310 then calculates (using Eq. 2, for example, or via a look-up table) the focal length of the optical system to zoom the object to a default distance $d_0$ and also determines (via a look-up table, for example), the zoom lens position corresponding to the focal point. (Alternatively, step 310 may comprise a unified step, for example, a single look-up table that correlates zoom distance to zoom lens position. The default distance do may then be used to directly determine the lens position.) In step 312, control unit determines whether a zoom voice input (for example, the spoken word "zoom") has been received. If so, in step 314 the control unit 100 sends control commands to the stepper motor 105 to move lenses to the determined position for the default zoom location.

After zooming the object to the default distance do, the control unit 100 determines in step 316 whether a voice command for zoom ticking has been entered. If so (for example, "zoom in" or "zoom out"), the control unit 100 in step 318 moves the lenses in or out to the next zoom tick position in the manner described above. After executing step 318 or if the determination in step 316 or 312 is "no", the processing returns to step 304, thus ensuring that the object gazed upon is the one that is zoomed when a voice command is received.

If it is determined in step 309 that the default zooming mode is not selected, the control unit 100 determines in step 322 whether a voice command is input giving a zoom distance d, for example, "ten feet". If so, then in step 324 the control unit 100 uses the input distance d and the gaze distance D (determined in steps 304–308) to calculate (using Eq. 4, for example, or via a look-up table) the focal length of the optical system to zoom the object to a input distance d and also determines (via a look-up table, for example), the zoom lens position corresponding to the focal point. (Alternatively, step 324 may comprise a unified step, for example, a single look-up table that correlates zoom distance to zoom lens position. The input distance d may then be used to directly determine the lens position.) In step 326, control unit 100 sends control commands to the stepper motor 105 to move lenses to the determined position for the input zoom distance. The processing then continues with step 316 for zoom ticking, as described above. (Step 316 is also the point where the control unit continues if the determination in step 322 is "no".)

While the invention has been shown and described with reference to certain preferred embodiments thereof, it will be understood by those skilled in the art that various changes in form and details may be made therein without departing from the spirit and scope of the invention as defined by the appended claims. For example, while the above exemplary embodiments described the invention in the context of a binocular system, one skilled in the art may readily adapt the invention to any other type of optical system that has a zoom feature, including, for example, a camera. In addition, the invention is not limited to zooming, but can be applied to any type of optical adjustment, for example, ordinary focusing of a camera, binoculars or other optical system.

What is claimed is:

1. An optical system comprising at least one adjustable optical element, a motor that interfaces with the at least one adjustable optical element to provide adjustment thereto, first and second eye position sensors that detect eye position data for a viewer's first and second eye, respectively, a control unit that receives position data from the at first and second eye position sensors and provides control signals to the motor, the control unit including:
   i) gaze tracking processing that determines gaze angles for each of the viewer's eyes from eye position data provided by the first and second eye position sensors,
   ii) gaze distance processing that determines the gaze distance of the viewer using the determined gaze angles,
   iii) optical element positioning processing that determines an adjustment position of the at least one optical element a function of the determined gaze distance,
   the control unit providing control signals to the motor to move the at least one adjustable optical element to the adjustment position.

2. The optical system as in claim 1, wherein the at least one adjustable optical element is at least one lens that provides a focus to a user of the optical system.

3. The optical system as in claim 2, wherein the at least one lens is a zoom lens.

4. The optical system as in claim 1, wherein the first and second eye position sensors are first and second cameras directed at the first and second eyes, respectively, of the viewer.

5. The optical system as in claim 4, wherein the eye position data of the first and second eyes detected by the first and second cameras, respectively, are images of the first and second eyes.

6. The optical system as in claim 5, wherein the gaze tracking processing of the control unit determines gaze angle for the each of the first and second eye using the position of a feature of the first and second eyes in the images.

7. The optical system as in claim 6, wherein the gaze distance processing determines the gaze distance D of the viewer according to the equation $$D = De/(\tan \alpha 1 = \tan \alpha 2)$$

wherein De represents the distance between the eyes of the user, α1 is the gaze angle of the first eye determined by the control unit and α2 is the gaze angle of the second eye determined by the control unit.

8. The optical system as in claim 1, wherein the optical element positioning processing determines a default distance from the gaze distance of the viewer, the adjustment position of the at least one optical element being a function of the default distance.

9. The optical system as in claim 8, wherein the at least one optical element is a zoom lens, the default distance is a default zoom distance to which the gaze distance is zoomed, the adjustment position being the location of the at least one optical element that that zooms an object at the gaze distance to the default zoom distance.

10. The optical system as in claim 9, wherein the control unit automatically provides control signals to the motor to move the at least one adjustable optical element to the adjustment position without user input.

11. The optical system as in claim 10, wherein the control unit controls the motor to provide a further adjustment of the zoom lens to subsequent zoom tick positions upon detection of a voice command of the viewer.

12. The optical system as in claim 1, wherein the optical element positioning processing receives an input distance from the viewer, the adjustment position of the at least one optical element being a function of the input distance.

13. The optical system as in claim 12, wherein the at least one optical element is at least one zoom lens, the input distance is a zoom distance to which the user desires the gaze distance to be zoomed, the adjustment position being the location of the at least one zoom lens that zooms an object at the gaze distance to the input zoom distance.

14. The optical system as in claim 13, wherein the control unit provides control signals to the motor to move the at least one zoom lens to the location that zooms an object at the gaze distance to the input zoom distance.

15. The optical system as in claim 13, wherein the control unit receives the input zoom distance from the viewer by voice input.

16. The optical system as in claim 13, wherein the control unit controls the motor to provide a further adjustment of the zoom lens to subsequent zoom tick positions upon detection of a voice command of the viewer.

* * * * *